United States Patent [19]

Stock

[11] Patent Number: 4,976,135
[45] Date of Patent: Dec. 11, 1990

[54] APPARATUS AND METHOD FOR DETECTING GAS COMPONENTS

[75] Inventor: Burkhard Stock, Lubeck, Fed. Rep. of Germany

[73] Assignee: Dragerwerk Aktiengesellschaft, Lubeck, Fed. Rep. of Germany

[21] Appl. No.: 363,497

[22] Filed: Jun. 8, 1989

[30] Foreign Application Priority Data

Feb. 18, 1989 [DE] Fed. Rep. of Germany ....... 3904994

[51] Int. Cl.$^5$ ........................................... G01N 31/00
[52] U.S. Cl. .................................................... 73/23.2
[58] Field of Search ............................... 73/23, 864.81; 422/83–88, 90–92, 98; 128/716, 719; 338/34

[56] References Cited

U.S. PATENT DOCUMENTS

| | | | |
|---|---|---|---|
| 3,940,251 | 2/1976 | Jones et al. | 422/84 |
| 4,346,584 | 8/1982 | Boehringer | 73/23 |
| 4,485,665 | 12/1984 | Norman | 422/87 |
| 4,688,015 | 8/1987 | Kojima et al. | 338/310 |
| 4,713,646 | 12/1987 | Sumano et al. | 338/34 |

Primary Examiner—Robert Raevis
Attorney, Agent, or Firm—McGlew and Tuttle

[57] ABSTRACT

A device for the transport of a gas sample into the measuring chamber of a detector for the determination of the portion of a component in a gas, and in particular of alcohol in respiratory air, includes a piston-cylinder unit serves as the transport element. The sample is used as completely as possible for the signal analysis of the sensor at the beginning of the sampling process. The measuring-sensitive surface of the sensor comprises a part of the wall of the cylinder chamber of the transport unit which serves as the measuring chamber. The path on which the sample is guided between the inlet and the cylinder chamber is defined by a deviation baffle provided along the measuring-sensitive surface of the sensor.

6 Claims, 1 Drawing Sheet

APPARATUS AND METHOD FOR DETECTING GAS COMPONENTS

FIELD AND BACKGROUND OF THE INVENTION

The invention relates in general to gas detectors and in particular to a new and useful device for the transport of a gas sample into a measuring chamber of a detector for the determination of the share of a component in a gas.

The invention refers particularly to alcohol in respiratory air, wherein a piston-cylinder unit serves as the transport element which transports the sample from a gas source through an inlet into the measuring chamber connected to a sensor by means of a flow-connection. Furthermore, a measuring process for the above is given.

German Patent No. 20 35 982 describes such a device with a piston-cylinder unit having a respiration mouth piece for the gas supply from which a sample to be measured is taken by means of a secondary flow, swirled in the cylinder chamber and fed into an analysis device by means of a scavenging stroke. In this known device it is disadvantageous that during the taking in of the air sample from the supply gas, molecules are adsorbed or even condensed on the cylinder wall and therefore they do not reach the detector during the scavenging stroke. Furthermore, once the scavenging stroke is executed, a part of the sample remains in the cylinder chamber and/or in the supply lines leading to the detector, thus it cannot be analyzed and the measuring result is incorrect with a tendency to showing quantitative detection results which are too low.

Furthermore, using piston-cylinder units as transporting elements have the disadvantage that the relatively large friction coefficient between the piston and the cylinder leads to a considerable output loss during operation. This is particularly undesirable when battery-operated devices are employed. The relatively large friction coefficient is mainly determined by the fact that the piston and the cylinder have to be sealed off against each other in the best manner possible in order to prevent leaks or the intake of secondary air.

Another device according to GB-A 2 044 462 has a transport element which leads the sample past the detector during the intake process. Herein it is disadvantageous that not all the molecules have enough time to react with the sensor during the intake process in order to make a contribution to a detection signal. The part of the sample not reacting with the sensor depends on the speed of reaction on the sensitive surface of the sensor in relation to the pumping speed.

SUMMARY OF THE INVENTION

The present invention provides a testing device in which the sample is used as completely as possible for a signal analysis by a sensor and without major output losses.

According to the invention, the sensitive surface of the sensor represents a part of the cylinder chamber wall forming the measuring chamber of the transport unit, and in the course of the measuring sample path between the inlet and the sensed volume a deviation baffle along the sensitive surface of the sensor is provided.

The advantage of the invention is that a more intensive reciprocal action or interaction between the gas sample and the sensor is achieved. During the pumping process the sample molecules have a sufficient period of dwell at the sensitive surface, so that the major part of the components to be detected has reacted with the sensor before it reaches the cylinder chamber. Once the intake stroke of the transport element is completed, only a small number of molecules to be detected remain in the cylinder chamber, which diffuse to the measuring surface during the standstill of the piston and make a contribution to the measuring signal. Thus a complete use of the sample at a high reaction speed is achieved by leading the sample along the measuring surface, as larger diffusion paths in the pumping chamber are relevant only for a small fraction of the molecules in the cylinder chamber. This deviation baffle is particularly advantageous when an electro-chemical sensor is used for the detection which contains e.g. sulfuric acid or brown oil of vitriol as an electrolyte. In this case the steam contained in the respiratory air after exhalation is absorbed while it passes the sensor surface (drying of the sample), so that a condensation at low temperatures in the pump chamber is avoided.

A particularly simple execution of a deviation path is realized by having the inlet open into a pre-chamber to the cylinder chamber. The pre-chamber has a measuring surface of the sensor and a non-movable or rigid face wall of the cylinder chamber has an opening as a part of its walls. A board partly encircles the opening and runs along the periphery of the measuring surface and forms the deviation baffle. Once the intake of the sample and the resting of the piston in its end position are terminated, the remaining molecules to be detected can directly diffuse from the cylinder chamber through the opening to the measuring surface, so that a complete usage of the sample is provided e.g. for an amperometric analysis. Due to the short diffusion paths the reaction speed remains high and the measuring time short.

To achieve a better sealing of piston and cylinder at as little adhesive friction as possible, it is advantageous to have the piston, which is pressed from graphitized coal dust, run in a glass cylinder. The advantage is that the lubricating properties of graphite have a very low friction coefficient even with the most exact calibration of the glass-graphite combination possible, thus resulting in low friction at a high degree of tightness or sealing. By this means a high degree of efficiency of the pump is achieved, which is required in battery operated devices. Further results are a long working life due to the least wear possible and a good closing-off of the sensor from the environment even when the piston is resting. As glass and graphite have the same coefficient of expansion, no temperature stabilization will be necessary for the transport elements even with changing temperatures of environment and operation. Glass and graphite are chemically inert, so that there is no danger of corrosion by the components in the samples or due to chemicals possibly contained in the measuring sensor, as e.g. sulfuric acid when an electro-chemical sensor is employed. An equally accurate sealing and fitting is provided by a piston-cylinder combination made of glass, wherein the running surfaces are ground-in.

A process for the measuring of a component in a gas sample, in particular for the determination of the alcohol contents in the respiratory air by means of a described device comprises causing the piston to execute an intake stroke by means of which the sample gas is led through the inlet, along a deviation baffle, over a measuring surface and into a cylinder chamber where it remains for a determinable period of dwell. This process reduces the measuring time as the major part of the sample reacts quickly and can be analyzed during the short intake stroke if e.g. the building-up rate of the measuring signal is measured by the sensor, and only a small amount of the sample remains, which can be detected by the sensor in a relatively short diffusion time for the purpose of an integrating quantitative determination (amperometrical measuring process).

After the analysis during the period of dwell the piston executes an exhaust stroke in order to evacuate the analyzed sample gas out of the inlet. This exhaust stroke does not lead to a signal at the sensor distorting the measuring result, as by now all the molecules present from the last sample have been used in reaction with the sensor, so that the sample gas is free of the molecules to be detected and can therefore be simply scavenged through the inlet as an inert waste gas. This makes complicated and mechanically vulnerable valve direction controls unnecessary.

Accordingly, it is an object of the invention to provide a method of testing for components of gases comprising withdrawing a sample of the gas and passing over a measuring surface and baffling the surface so as to extend the path of the gas which is in contact with the measuring surface.

A further object of the invention is to provide a device for indicating the presence of a gas component in a gas sample collected in a sampling tube which comprises a sensor housing having a test chamber therein, a measuring surface disposed on the interior of said housing extending along said test chamber, a piston and cylinder unit connected to the sampling tube through said test chamber, guide means which is connected to the piston to reciprocate it and to cause the drawing in of the gas sample from the sampling tube and to move it into the test chamber and which includes baffle means in the chamber which are arranged so as to extend the path of travel of the gas in the chamber to increase its contact with the measuring surface.

A further object of the invention is to provide a testing device which is simple in design, rugged in construction and economical to manufacture.

While specific embodiments of the invention have been shown and described in detail to illustrate the application of the principles of the invention, it will be understood that the invention may be embodied otherwise without departing from such principles.

DESCRIPTION OF THE PREFERRED EMBODIMENTS

Figure 1:
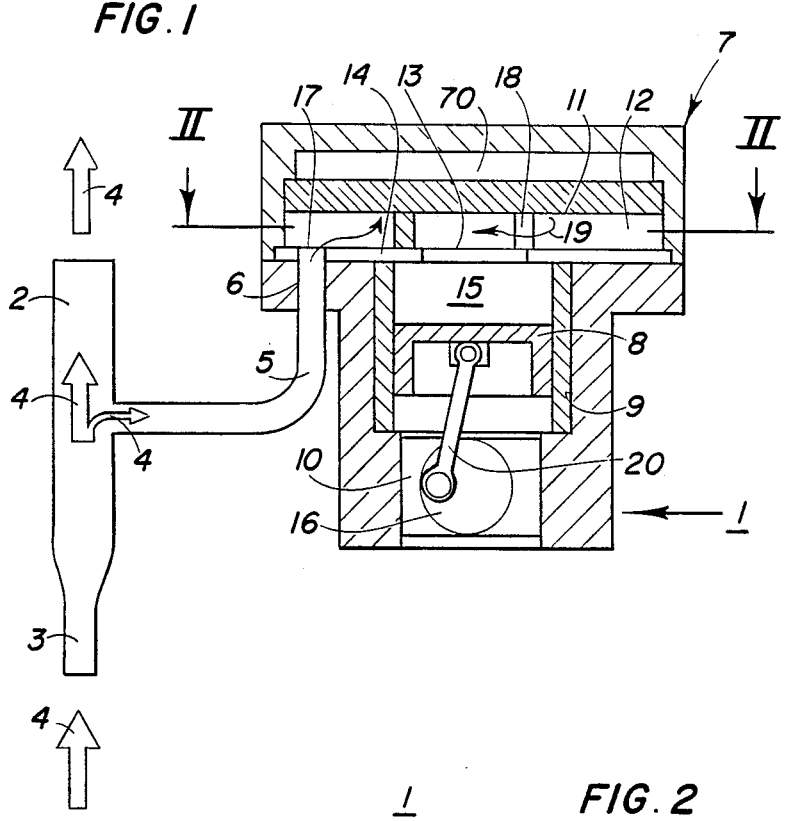
FIG. 1 is a sectional view of a detector with a sensor and a piston-cylinder unit, constructed in accordance with the invention.

Referring to the drawings in particular, the invention embodied therein comprises a method and apparatus for testing to determine the components of a gas which is directed in a direction of arrows 4 through a sampling tube 2. In accordance with the invention, a sample of the gas is withdrawn from the tube through a feed tube or bypass 5 and the gas is passed into association with a measuring surface 11 defined in a sensor generally designated 7 which has a housing which also encloses a drive unit in the form of a piston 8 movable in a cylinder 9 which is part of the housing of the sensor 7. In accordance with a feature of the invention the path of movement of the sample is through a sample inlet 17 of the sensor 7 and around in a path which contacts a measuring surface 11 for a very large area. With the invention, the baffle or board 18 is arranged in a chamber or pre-chamber 12 defined over a face board 14 and it ensures the flow of the sample gases in the paths 19,19' indicated in FIG. 2 into the cylinder chamber 15.

FIG. 1 shows a detector, generally designated 1 for the determination of the share of a component in a gas, in particular of the parts of alcohol in respiratory air. The embodiment of the invention is explained by means of the examination of the parts of alcohol in the respiratory air. A sampling device such as a tube 2 has a mouthpiece 3 for a tested person (not shown) who takes the mouthpiece into his mouth and he blows respiratory air in the direction of the arrows 4 through the sampling device 2. A heated tubular sampling line 5 branches off from the sampling device and leads into the housing 6 of the detector 1.

The detector 1 comprises a sensor generally designated 7, a piston 8, movable in a cylinder 9 which is reciprocated by a driving motor 10. The sensor 7 has a measuring surface 11 which separates an inner chamber 70 containing an electrolyte from a pre-chamber 12. The pre-chamber 12 is an extension of a cylinder chamber 15.

Typically the measuring surface 11 is a membrane which is permeable by the alcohol fumes. The pre-chamber 12 is separated from the cylinder unit 9 and the cylinder chamber 15 by a face wall 14 having an opening 13. The cylinder chamber 15 is changed by the movements of the piston 8. In the drawing the piston 8 is about to reach the top dead center, which is determined by an eccentric 16 on the driving motor 10. The piston 8 is moved in the cylinder 9 by means of the connecting rod 20. For the sample intake the piston 8 is moved to its bottom dead center by the motor 10 and remains there for a certain period of time. During the intake-stroke of the piston 8 a sample of the respiratory air flowing through the sampling device 2 flows through the sampling tube 5 into the pre-chamber 12 via an inlet 17 and from there around a board 18 forming a deviation baffle through the opening 13 and into the cylinder chamber 15. During the intake stroke the sample in the pre-chamber 12 flows along the measuring surface 11 of the sensor 7, preferably extensively along the full expansion of its surface. During this time the essential transformation of the alcohol in the respiratory air into a measuring signal takes place. During the short period of dwell in the cylinder chamber 15 the remainder of the alcohol not yet transformed is enclosed in the analysis by diffusion to the measuring surface 11. By this means the sample is transformed into a measuring signal rather speedily resulting in a short reaction time of the detector 1. Even for amperometrical measuring can the complete transformation of the sample gas into a measuring signal be achieved in a relatively short period of time.

Figure 2:
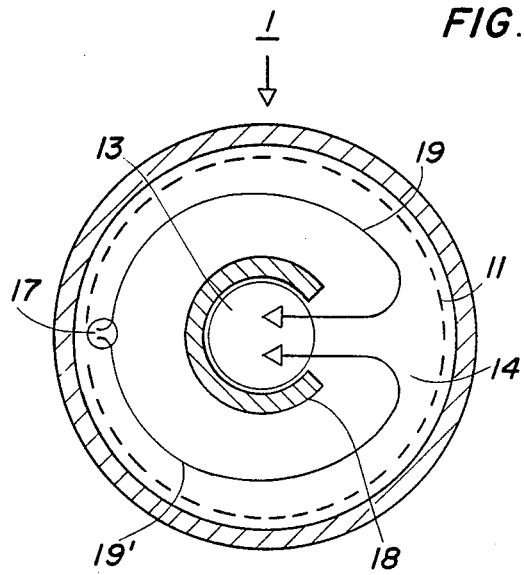
FIG. 2 is a section of the pre-chamber with the sensor removed taken along the line II—II of FIG. 1.

The FIG. 2 view of the housing 1 shows the opened pre-chamber 12 and onto the face wall 14 of the transport unit including the piston 8 and the cylinder 9 having the opening 13 and receiving the board 18. Due to the opening 13 a part of the face of the piston 8 is visible. The board 18 encircles the opening 13 along its periphery, leaving a section opposite the inlet 17 open, however. The contour of the measuring surface 11 is shown as a broken line on the face wall 14. It indicates that the respective measuring surface 11 lies close in this section when the sensor is in place. While the sample flows from the inlet 17 into the pre-chamber 12 the gas molecules are sucked along the path 19,19' into the cylinder chamber 15. Herein they inevitably flow along a large part of the measuring surface 11.

While specific embodiments of the invention have been shown and described in detail to illustrate the application of the principles of the invention, it will be understood that the invention may be embodied otherwise without departing from such principles.

What is claimed is:

1. A device for indicating the presence of a gas component in a gas sample which is collected in a sampling tube, comprising a sensor having a housing with a measuring chamber therein, a measuring surface disposed on the interior of said housing extending along said measuring chamber, a piston and cylinder unit connected to the sampling tube through said measuring chamber, drive means to reciprocate said piston in said cylinder to draw a gas sample from the sampling tube and move it into said measuring chamber, and baffle means in said measuring chamber extending the route of travel of the gas sample in said chamber so as to increase the time said gas sample is in contact with said measuring surface wherein said measuring chamber includes an inlet connected to the sampling tube and a face wall overlying said cylinder having an opening into said cylinder above said piston, said inlet being connected into said measuring chamber, and said baffle means defined between said inlet and said cylinder defining a long tortuous flow for the gas sample, said baffle means including a curved board disposed between said measuring surface and said face wall defining a flow path from said inlet around each side of said curved board into said cylinder.

2. A device according to claim 1, wherein said piston is made of a graphite coal dust with cylinder comprising a glass cylinder.

3. A device according to claim 1, wherein said piston is made of glass and said cylinder is made of ground in glass.

4. A device for indicating the presence of a gas component in a gas sample comprising:
    a sensor;
    a measuring surface within said sensor;
    a face board spaced from said measuring surface to form a pre-chamber therewith, said face board having a central opening and an inlet opening for drawing said gas sample into said pre-chamber;
    a baffle extending between said measuring surface and said face board partially surrounding said central opening and positioned between said inlet opening and said central opening;
    a cylinder positioned adjacent said face board encircling said central opening; and
    a piston reciprocally mounted with said cylinder.

5. A method of sampling a gas comprising the steps of:
    sucking a gas sample through a pre-chamber and into an adjacent cylinder;
    directing the gas sample to flow around a baffle while passing through the pre-chamber;
    measuring a component of the gas sample with a measuring surface forming part of the pre-chamber primarily during passage of the gas sample through the pre-chamber.

6. A method of sampling a gas as in claim 5 wherein the step of measuring further comprises the step of:
    measuring a component of the gas sample amperometrically.

* * * * *